United States Patent
Majeed et al.

(10) Patent No.: US 11,925,606 B2
(45) Date of Patent: Mar. 12, 2024

(54) COMPOSITIONS FOR MANAGING CHRONIC OBSTRUCTIVE PULMONARY DISEASE

(71) Applicants: Muhammed Majeed, Bangalore (IN); Kalyanam Nagabhushanam, East Windsor, NJ (US); Sarang Bani, Bangalore (IN); Anjali Pandey, Bangalore (IN)

(72) Inventors: Muhammed Majeed, Bangalore (IN); Kalyanam Nagabhushanam, East Windsor, NJ (US); Sarang Bani, Bangalore (IN); Anjali Pandey, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 380 days.

(21) Appl. No.: 17/151,121

(22) Filed: Jan. 16, 2021

(65) Prior Publication Data
US 2021/0220290 A1    Jul. 22, 2021

Related U.S. Application Data

(60) Provisional application No. 63/126,920, filed on Dec. 17, 2020, provisional application No. 62/962,343, filed on Jan. 17, 2020.

(51) Int. Cl.
*A61K 31/12* (2006.01)
*A61P 11/00* (2006.01)

(52) U.S. Cl.
CPC .............. *A61K 31/12* (2013.01); *A61P 11/00* (2018.01)

(58) Field of Classification Search
CPC .............................. A61K 31/12; A61P 11/00
See application file for complete search history.

(56) References Cited

PUBLICATIONS

Istyastono et al., Oriental Journal of Chemistry, 2016, 32(1), 275-282.*

* cited by examiner

*Primary Examiner* — Sun Jae Yoo

(57) ABSTRACT

The invention discloses a composition comprising not less than 20% w/w bisdemethoxycurcumin for regeneration of alveolar cells damaged in emphysematous conditions and for the therapeutic management of chronic obstructive pulmonary disease and acute respiratory distress syndrome. The composition further comprises 10-35% w/w demethoxycurcumin and 10-45% w/w curcumin. The composition is very suitable for treating COPD and ARDS due to viral infections, specifically COVID 19 and for improving lung function during prognosis.

12 Claims, 12 Drawing Sheets
(1 of 12 Drawing Sheet(s) Filed in Color)

Normal Control

COPD Control

BDMC- 25mg/kg

BD3 Complex- 100mg/kg

COMPOSITIONS FOR MANAGING CHRONIC OBSTRUCTIVE PULMONARY DISEASE

CROSS-REFERENCE TO RELATED PATENT APPLICATIONS

This is a non-provisional US patent application claiming priority from U.S. Provisional application 62/962,343, filed on 17 Jan. 2020, and U.S. Provisional application No. 63/126,920, filed on 17 Dec. 2020, the details of which are being incorporated herein by reference.

FIELD OF INVENTION

The present invention relates to composition for the management of Chronic obstructive pulmonary disease. More specifically, the invention pertains to compositions comprising bisdemethoxycurcumin for regeneration of alveoli and for the management of Chronic obstructive pulmonary disease and Acute respiratory distress syndrome.

BACKGROUND OF THE INVENTION

Chronic obstructive pulmonary disease (COPD) is a chronic inflammatory lung disease that causes obstructed airflow from the lungs. It is typically caused by long-term exposure to irritating gases like cigarette smoke, fuel combustion, viral infections or particulate matter. Emphysema and chronic bronchitis are the two most common conditions that contribute to COPD.

Emphysema is a condition in which the alveoli at the end of the smallest air passages (bronchioles) of the lungs are destroyed. Emphysema is defined by the American Thoracic Society as follows: "Emphysema is a condition of the lung characterized by abnormal, permanent enlargement of the air spaces distal to the terminal bronchiole, accompanied by destruction of their walls." It is a major component of COPD and is characterized by alveolar extracellular matrix destruction, reduction in the alveolar capillary exchange area, which leads to partially reversible airflow obstruction. This causes destruction of the fragile walls and elastic fibers of the alveoli causing collapse in the small airways collapse impairing airflow out of lungs. The signs and symptoms include Shortness of breath, especially during physical activities, Wheezing, Chest tightness, A chronic cough that may produce mucus, Frequent respiratory infections, Lack of energy, Unintended weight loss (in later stages), Swelling in ankles, feet or legs (Thurlbeck et al., Emphysema: Definition, Imaging, and Quantification, Benjamin Felson lecture, AJR 1994; 163:1017-1025), Evidence indicated marked difference in the pathological features of normal and COPD lungs. In a healthy individual, cells respond to mild damage through exogenous ROS by activating repair mechanisms such as antioxidant, DNA-repair and autophagy. If the damage is too great, cells will undergo senescence thus preventing oncogenic changes. Stem cell renewal plays an important role in tissue regeneration and healing. However, in a person affected with COPD. excessive ROS results in increased damage to lung cells aggravated by a defective repair mechanism. Increased senescent cells further stimulate inflammation, alveolar destruction, endothelial dysfunction increasing the risk of oncogenic changes. ROS also results in loss of stem cells renewal by induced loss of quiescence and stem cell senescence. This leads to loss in tissue regeneration (Mercado et al., Accelerated ageing of the lung in COPD: new concepts, Thorax 2015; 70:482-489. doi:10.1136/thoraxjnl-2014-206084). In addition to emphysematous COPD, non-emphysematous COPD is also prevalent (Occhipinti et al., Emphysematous and Nonemphysematous Gas Trapping in Chronic Obstructive Pulmonary Disease: Quantitative CT Findings and Pulmonary Function, Radiology: 2018, Volume 287: Number 2-683-692).

Acute respiratory distress syndrome (ARDS) is also observed in the late stages of COPD. It is characterized by dyspnea, severe hypoxemia, decreased lung compliance, and diffuse bilateral pulmonary infiltrates. There are typically three phases in the pathology of ARDS: exudative, proliferative, and fibrotic. Type I alveolar cells are irreversibly damaged and there is deposition of proteins, fibrin, and cellular debris, producing hyaline membranes in the denuded space. Injury to the surfactant-producing type II cells also contributes to alveolar collapse. The type II cells proliferate with some epithelial cell regeneration, fibroblastic reaction, and remodelling in the proliferative phase (Udobi et al., Acute Respiratory Distress Syndrome, Am Fam Physician. 2003 Jan. 15; 67(2):315-322). Thus, there is alveolar degeneration in both COPD and ARDS.

Recently, it was observed that COPD may be a risk factor for more severe COVID-19 disease (Alqahtani et al. Prevalence, severity and mortality associated with COPD and smoking in patients with COVID-19: a rapid systematic review and meta-analysis. PLoS One 2020; 15: e0233147). An analysis of comorbidities in 1590 COVID-19 patients across China found that COPD carried an odds ratio of 2.681 (95% CI 1.424-5.048; p=0.002) for ICU admission, mechanical ventilation or death, even after adjustment for age and smoking; 62.5% of severe cases had a history of COPD (compared with only 15.3% in non-severe cases) and 25% of those who died were COPD patients (compared with only 2.8% in those who survived) (Leung et al., COVID-19 and COPD, European Respiratory Journal 2020 56: 2002108; DOI: 10.1183/13993003.02108-2020). This shows that COPD is the most prominent cause in the pathology of COVID-19.

Typically, the pathogenesis of COVID-19 can be divided into three phases: First phase of the disease is in the nose, second phase in conducting airways, the bronchi and bronchioles and the third phase of the disease is the lethal phase, as the infection spreads into the gas exchange portion of the lung and infects alveolar type II cells.

The alveolar involvement is characterized by profound hypoxia, and Inflammatory flooding. Along with the damage to Alveolar type I and type II cells, there is extensive damage to the endothelium. This results in leakage of fibrinogen and other plasma proteins into the alveolus that impair the ability of surfactant to absorb to the surface and lower surface tension. Thus, alveolar degeneration play a vital role in the pathology of viral infections like COVID 19.

Alveolar regeneration therapies are now being considered as an effective treatment for the management of COPD and ARDS. The ability of adult mammals to regenerate organs seems to be limited to only the liver. However, on a tissue, rather than a whole organ level, mammals can continually replace cells composing epidermis, gut endoderm, blood, neurons etc. It was recently discovered that retinoic acid can induce the regeneration of lung alveoli in the experimentally damaged adult rat lung. The present invention discloses natural and novel compositions for the regeneration of alveoli and for managing COPD and ARDS.

There are many natural compounds that are currently being used for managing COPD. Turmeric compositions comprising Curcumin are reported to be effective in ameliorating the symptoms of COPD and ARDS. The following prior art documents disclose the use of turmeric, specifically curcumin in managing COPD 1. Tang et al., Curcumin ameliorates chronic obstructive pulmonary disease by modulating autophagy and endoplasmic reticulum stress through regulation of SIRT1 in a rat model, Journal of International Medical Research, 2019, Vol. 47(10) 4764-4774.
2. Jawed et al., Effect of Turmeric on Mosquito Coil Induced Emphysema in Rat Lungs, JIIMC 2018 Vol. 13, No. 3, 141-145.
3. Moghaddam et al., Curcumin inhibits COPD-like airway inflammation and lung cancer progression in mice, Carcinogenesis vol. 30 no. 11 pp. 1949-1956, 2009.
4. Santana et al., Evidences of Herbal Medicine-Derived Natural Products Effects in Inflammatory Lung Diseases, Mediators of Inflammation, Volume 2016, Article ID 2348968, 14 pages, http://dx.doi.org/10.1155/2016/2348968.
5. Butler and Kaifer, Herbs and Supplements for COPD (Chronic Bronchitis and Emphysema), Healthline, Updated on Aug. 20, 2018, healthline.com/health/copd/herbs-supplements, accessed 5 Jan. 2021

Tumeric has different compounds of which curcumin, dimethoxy curcumin and bisdemethoxycurcumin are the major players. The biological properties of curcumin, bisdemethoxycurcumin and demethoxycurcumin vary in different diseases and the effect of bidemethoxycurucmin in managing COPD and related functions is not evaluated. The present invention discloses the biological potential of a composition comprising bisdemethoxycurcumin in alveolar regeneration and in managing symptoms of COPD and ARDS.

It is the principle object of the invention to disclose a comprising not less than 20% w/w bisdemethoxycurcumin for use in regeneration of alveolar cells in emphysema.

It is another object of the invention to disclose a composition comprising not less than 20% w/w bisdemethoxycurcumin for use in managing the symptoms of chronic obstructive pulmonary disease.

It is yet another object of the invention to disclose a composition comprising not less than 20% w/w bisdemethoxycurcumin for use in preventing the progression of chronic obstructive pulmonary disease to acute respiratory distress syndrome.

The present invention satisfies the above mentioned objectives and provides related advantages.

SUMMARY OF THE INVENTION

In a most preferred embodiment, the invention discloses a method for regeneration of alveolar cells in mammals with emphysema, said method comprising step of administering a composition comprising not less than 20% w/w bisdemethoxycurcumin to said mammals to bring about a reduction in features of emphysema In another preferred embodiment, the invention discloses a method of therapeutic management of chronic obstructive pulmonary disease in mammals, said method comprising step of administering a composition comprising not less than 20% w/w bisdemethoxycurcumin to said mammals to bring about a reduction in features and symptoms of chronic obstructive pulmonary disease.

In another preferred embodiment, the invention discloses a method of preventing the progression of chronic obstructive pulmonary disease to acute respiratory distress syndrome in mammals, said method comprising step of administering a composition comprising not less than 20% w/w bisdemethoxycurcumin to said mammals to bring about a reduction in features and symptoms of chronic obstructive pulmonary disease.

Other features and advantages of the present invention will become apparent from the following more detailed description, taken in conjunction with the accompanying images, which illustrate, by way of example, the principle of the invention.

DESCRIPTION OF DRAWINGS

The patent or application file contains at least one drawing executed in color. Copies of this patent or patent application publication with color drawing(s) will be provided by the office upon request and payment of the necessary fee.

FIG. 7 B is the graphical representation showing the dose dependant decrease in IL-6 levels in COPD mice treated with varying doses (mg/kg bodyweight) of a composition comprising bisdemethoxycurcumin (BD3 complex) compared to curcumin C3 complex.

FIG. 8 B is the graphical representation showing the dose dependant decrease in CXCL8 levels in COPD mice treated with varying doses (mg/kg bodyweight) of a composition comprising bisdemethoxycurcumin (BD3 complex) compared to curcumin C3 complex.

FIG. 9 B is the graphical representation showing the dose dependant decrease in LDH levels in COPD mice treated with varying doses (mg/kg bodyweight) of a composition comprising bisdemethoxycurcumin (BD3 complex) compared to curcumin C3 complex.

DESCRIPTION OF PREFERRED EMBODIMENTS

Figure 1A:
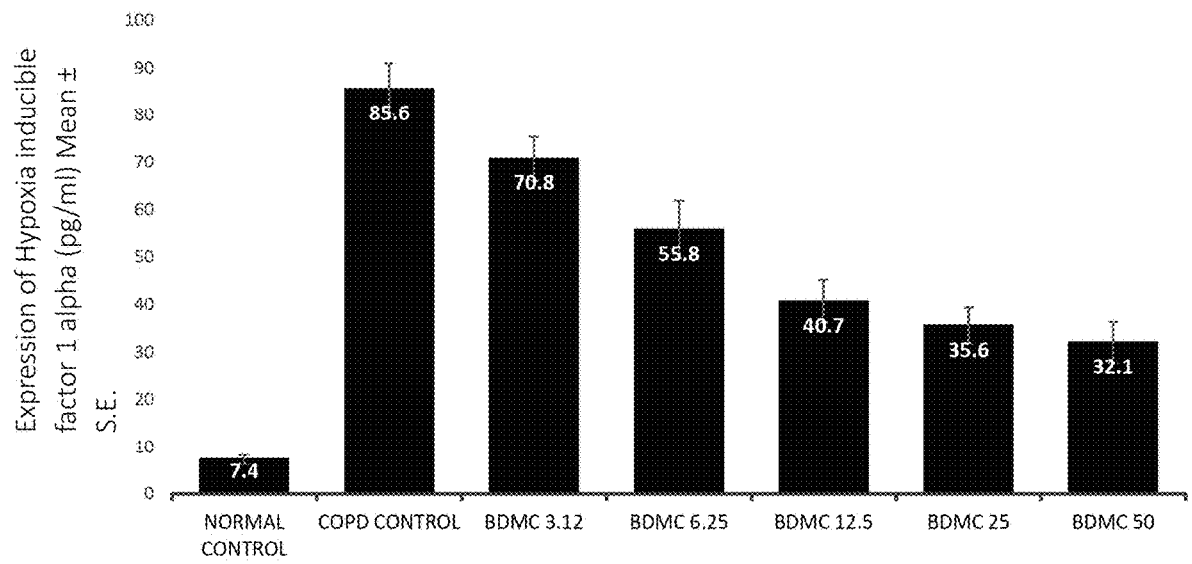
FIG. 1A is the graphical representation showing the dose dependant decrease in HIF-1α levels in COPD mice treated with varying doses (mg/kg bodyweight) of bisdemethoxycurcumin (BDMC) compared to normal and COPD control groups.

In a most preferred embodiment, the invention discloses a method for regeneration of alveolar cells in mammals with emphysema, said method comprising step of administering a composition comprising not less than 20% w/w bisdemethoxycurcumin to said mammals to bring about a reduction in features of emphysema. In a related embodiment, the composition further comprises 10-35% w/w demethoxycurcumin and 10-45% w/w curcumin. In another related embodiment, the features of emphysema are selected from the group consisting of hypoxia, decreased levels of lung surfactant proteins, increased permeability of the alveolar-capillary barrier, inflammation, increased accumulation and recruitment of neutrophils, elevated alveolar pressure, increased oxidative stress, elevated inflammatory cytokines and chemokines, increased numbers of activated T lymphocytes and muscle damage. In yet another related embodiment, emphysema is induced by enzymes, viruses, bacteria, smoke and particulate irritants. In another related embodiment the mammal is human.

In another preferred embodiment, the invention discloses a method of therapeutic management of chronic obstructive pulmonary disease in mammals, said method comprising step of administering a composition comprising not less than 20% w/w bisdemethoxycurcumin to said mammals to bring about a reduction in features and symptoms of chronic obstructive pulmonary disease. In a related embodiment, the composition further comprises 10-35% w/w demethoxycurcumin and 10-45% w/w curcumin. In another related embodiment, the chronic obstructive pulmonary disease is emphysematous and non-emphysematous. In another related embodiment, the features of chronic obstructive pulmonary disease are selected from the group consisting of hypoxia, decreased levels of lung surfactant proteins, increased permeability of the alveolar-capillary barrier, inflammation, increased accumulation and recruitment of neutrophils, elevated alveolar pressure, increased oxidative stress, elevated inflammatory cytokines and chemokines, increased numbers of activated T lymphocytes and muscle damage. In another related embodiment, symptoms of chronic obstructive pulmonary disease are selected from the group consisting of shortness of breath, especially during physical activities, wheezing, chest tightness, chronic cough that may produce mucus, respiratory infections, lack of energy, unintended weight loss, and swelling in ankles, feet or legs. In yet another related embodiment, chronic obstructive pulmonary disease is induced by enzymes, viruses, bacteria, smoke and particulate irritants. In another related embodiment the mammal is human.

In another preferred embodiment, the invention discloses a method of preventing the progression of chronic obstructive pulmonary disease to acute respiratory distress syndrome in mammals, said method comprising step of administering a composition comprising not less than 20% w/w bisdemethoxycurcumin to said mammals to prevent onset acute respiratory syndrome by bringing about a reduction in features and symptoms of chronic obstructive pulmonary disease. In a related embodiment, the composition further comprises 10-35% w/w demethoxycurcumin and 10-45% w/w curcumin. In another related embodiment, the chronic obstructive pulmonary disease is emphysematous and non-emphysematous. In another related embodiment, the features of chronic obstructive pulmonary disease are selected from the group consisting of hypoxia, decreased levels of lung surfactant proteins, increased permeability of the alveolar-capillary barrier, inflammation, increased accumulation and recruitment of neutrophils, elevated alveolar pressure, increased oxidative stress, elevated inflammatory cytokines and chemokines, increased numbers of activated T lymphocytes and muscle damage. In another related embodiment, symptoms of chronic obstructive pulmonary disease are selected from the group consisting of shortness of breath, especially during physical activities, wheezing, chest tightness, chronic cough that may produce mucus, respiratory infections, lack of energy, unintended weight loss, and swelling in ankles, feet or legs. In yet another related embodiment, chronic obstructive pulmonary disease is induced by enzymes, viruses, bacteria, smoke and particulate irritants. In another related embodiment the mammal is human.

The preferred embodiments of the invention are further described in the following illustrative examples

Example 1: Elastase-Induced Pulmonary Emphysema

Wistar rats were divided into experimental groups and received an intratracheal administration of porcine pancreatic ELT (48.0 U/mg protein; at 0, 20, or 160 U dissolved in 100 μl of Dulbecco's calcium and magnesium-free phosphate-buffered saline under anesthesia. Twenty-one days after the intratracheal administration of ELT, various parameters in bronchoalveolar lavage fluid (BALF), the concentrations of proinflammatory mediators and biochemical parameters in lung homogenates, and lung function in the rats were evaluated (Inoue et al., Extensive analysis of elastase induced Pulmonary Emphysema in Rats: ALP in the Lung, a New Biomarker for Disease Progression? J. Clin. Biochem. Nutr., 46, 168-176, March 2010)

The rats were divided into the following groups:

| Group | Description |
|---|---|
| Group 1 | Normal control |
| Group 2 | COPD control |
| Group 3 | BDMC administered at 3.12 mg/kg bodyweight |
| Group 4 | BDMC administered at 6.25 mg/kg bodyweight |
| Group 5 | BDMC administered at 12.5 mg/kg bodyweight |
| Group 6 | BDMC administered at 25 mg/kg bodyweight |
| Group 7 | BDMC administered at 50 mg/kg bodyweight |
| Group 8 | C3 complex administered at 100 mg/kg bodyweight |
| Group 9 | BD3 complex administered at 12.5 mg/kg bodyweight |
| Group 10 | BD3 complex administered at 25 mg/kg bodyweight |
| Group 11 | BD3 complex administered at 50 mg/kg bodyweight |
| Group 12 | BD3 complex administered at 100 mg/kg bodyweight |
| Group 13 | BD3 complex administered at 200 mg/kg bodyweight |
| Group 14 | Curcumin administered at 25 mg/kg bodyweight |
| Group 15 | DMC administered at 25 mg/kg bodyweight |

For clarity the definition of the compounds administered in the above group is provided below:
BDMC—bisdemethoxycurcumin (pure compound)
Curcumin C3 complex/C3 complex—a composition comprising 75-81% curcumin 15-19% demethoxy curcumin, and 2.2-6.5% bisdemethoxy curcumin.
BD3 complex—a composition comprising not less than 20% w/w bisdemethoxycurcumin, 10-35% w/w demethoxycurcumin and 10-45% w/w curcumin (as disclosed in U.S. provisional application No. 63/126, 920, which is incorporated herein by reference)
Curcumin—Pure curcumin
DMC—demethoxycurcumin (pure compound)
As an illustrative example, the concentration of BD3 complex used for the experiments is 32% w/w BDMC, 30% w/w DMC and 38% curcumin. However, a person skilled in the art would realise that the effects as shown in the following examples are applicable to the concentration of 20% w/w bisdemethoxycurcumin, 10-35% w/w demethoxycurcumin and 10-45% w/w curcumin.

Collection of BALF—The rats were anesthetized with sodium pentobarbital via intraperitoneal injection (50 mg/kg) and exsanguinated from the abdominal aorta. A cannula was inserted into the trachea and secured with a suture. Their lungs were lavaged twice with 10 ml of sterile saline at 37° C., which was instilled bilaterally by syringe. The fluid was harvested by gentle aspiration. The collected fluid was cooled and centrifuged at 300 g for 10 min the supernatant was collected for analysis (Inoue et al., Extensive analysis of elastase induced Pulmonary Emphysema in Rats: ALP in the Lung, a New Biomarker for Disease Progression? J. Clin. Biochem. Nutr., 46, 168-176, March 2010)

Lung Parameters

Surfactant Protein and Periostin were measured in BALF through commercially available ELISA kits. This assay employs the quantitative sandwich enzyme immunoassay technique. Antibody specific for SP-D was pre-coated onto a microplate. Standards and samples were pipetted into the wells and any SP-D present is bound by the immobilized antibody. After removing any unbound substances, a biotin-conjugated antibody specific for SP-D was added to the wells. After washing, avidin conjugated Horseradish Peroxidase (HRP) was added to the wells. Following a wash to remove any unbound avidin-enzyme reagent, a substrate solution was added to the wells and color develops in proportion to the amount of SP-D bound in the initial step. The color development is stopped and the intensity of the color is measured which is proportional to the amount of SP-D present Quantitation of the Levels of HIF-1 Alpha, 12/15 LOX, IL-6, CXCL-8 in the Lung Tissue Supernatants The lung of the animals was removed and rinsed with ice-cold isotonic saline. To the tissues was added 4 ml/g tissue of extraction buffer containing 1 mM phenylmethylsulfonyl fluoride, 1 mg/ml aprotinin and 0.05% Tween 20 in phosphate buffered saline. Tissues were homogenized on ice with a polytron and the homogenate was centrifuged at 5000 g for 15 min. Aliquots of the supernatant were separated and used for biochemical analysis. Supernatants were stored at −80° C. until cytokine analysis (Pandey et al., Multifunctional neuroprotective effect of Withanone, a compound from *Withania somnifera* roots in alleviating cognitive dysfunction. Cytokine 102 (2018) 211-221)

Collection of Serum for Measurement of IL17/IL23 and LDH-A

Blood was taken from the retro-orbital plexus of the animals. The sample was made to sit for 2 hours and centrifuged. Samples of the serum obtained from different groups of animals were prepared for the analysis of cytokines using commercially available kits based on sandwich and competitive ELISA technique according to the manufacturer's instructions. All cytokine concentrations were carried out by means of colorimetric measurement at 450 nm on an ELISA plate reader by interpolation from a standard curve (Pandey et al., Amelioration of Adjuvant Induced Arthritis by Apocynin. Phytother Res, 2009 October; 23(10):1462-8)

Immunohistochemical Detection of AT-2

The sections of Lungs were subjected for immunohistochemistry to demonstrate AT-2 cells using a Mouse Anti-Human Thyroid Transcription Factor 1 (TTF-1) (clone SPT24) M/s Master diagnostica, (Cat #MAD-000486QD-12) Granada.

Materials

Immunochemicals

1) Primary antibody: Mouse Anti-Human Thyroid Transcription Factor 1 (TTF-1) (clone SPT24) M/s Master diagnostica, (Cat #MAD-000486QD-12) Granada of 1:50 dilution.
2) Secondary antibody: Super Sensitive™ (SS) Polymer-HRP IHC Detection System, M/s Biogenex, USA, Anti mouse and Anti-rabbit secondary antibody
3) Section adhesive 3-aminopropyltriethoxy-silane (APES), Procured from Sigma chemicals, USA.
4) Hydrogen peroxide ($H_2O_2$) in methanol (3%), Three percent $H_2O_2$ in methanol was prepared by adding one ml of 30 percent $H_2O_2$ to 9 ml of methanol.
5) Antigen retrieval solution:
   a. 1 mM EDTA BUFFER (pH-8.4):
   b. 1 mM EDTA, pH 8.0
   c. EDTA 0.37 g
   d. Distilled water 1 L
   The pH was adjusted to 8.4 with IN NaOH. All the solutions were prepared freshly just before the use.
6) DAB plus substrate: 3,3-diamine benzidine tetrahydrochloride substrate was prepared freshly at the time of use by addition of 1 mg of 3,3-diamine benzidine tetrahydrochloride (Santacruz, USA) to 1 ml of 0.01 M PBS to which 12 µl of 3 percent $H_2O_2$ was added.
7) 0.01M phosphate buffer saline (pH-7.2): 10× concentration of 500 ml PBS was prepared by adding the following chemicals, Sodium chloride (MW 58.44) 40 g, Potassium Chloride (MW 74.56) 1 g, Disodium hydrogen orthophosphate (MW 141.96) 7.2 g, Potassium dihydrogen orthophosphate anhydrous (MW 136.09) 1 g, Distilled water 500 ml. Wash buffer of 1× concentration was prepared using 10×PBS by adding 25 ml of 10×PBS to 225 ml of distilled water. To this 125 µl Tween 20 was added and the pH was adjusted to 7.2.
8) Harris haematoxylin for nuclear staining: Harris haematoxylin was used for nuclear staining. Counter staining was carried out for 45 seconds.

Preparation of organosilane (APES) treated slides for IHC: The preparation was performed using the following steps:
1. The slides were placed on racks, washed thoroughly in soap water, rinsed in tap water and finally rinsed in distilled water and dried completely.
2. A 2% solution of 3-aminopropyltriethoxy-silane (APES) in acetone in a dry staining dish was prepared. The slides were immersed in the APES solution for 5-15 minutes.
3. The slides were rinsed in acetone and then rinsed in two changes of distilled water. Slides were allowed to dry at 37° C. for two hours and then stored at room temperature for further processing later.

Method

1. Tissue sections were mounted on 3-aminopropyltriethoxy-silane (APES) coated slides and dried at 37° C. for three hours. Later stored at 4° C. for further processing later.
2. The paraffin tissue sections were deparaffinized using xylene and rehydrated using descending grades of ethanol.
3. Endogenous peroxidase was blocked by covering the whole section with 3 percent of $H_2O_2$ in methanol (100 µl). This was incubated at room temperature for fifteen minutes and later washed with three changes of wash buffer.
4. Heat induced epitope retrieval (HIER) was carried out by immersing tissue sections in a cooker containing EDTA buffer (pH 8.4) and was heated for 6 minutes after maximum pressure was attained. Sections were allowed to cool down to room temperature for approximately 30 minutes and later washed with three changes of wash buffer.
5. Addition of primary antibody: Ready to use Mouse Anti-Human Thyroid Transcription Factor 1 (TTF-1) (clone SPT24) was added to cover the sections. Subsequently the sections were incubated at room temperature in humidified chamber for one hour and washed with wash buffer as mentioned earlier.
6. Addition of secondary antibody: Super Sensitive™ (SS) Polymer-HRP IHC Detection System, M/s Biogenex, USA, Anti mouse and Anti-rabbit secondary antibody was added to section and incubated at room temperature in humidified chamber for 30 minutes. After incubation sections were washed with PBS as mentioned earlier.
7. Addition of DAB plus substrate: Freshly prepared 3, 3-diamine benzidine tetrahydrochloride (DAB) with 3 percent $H_2O_2$ was poured to cover the sections. This was incubated for 15-20 minutes or until the desired stain intensity was achieved. Later the sections were washed again with three changes of distilled water.
8. Nuclear counter staining with Harris haematoxylin was carried out for 45 seconds. The sections were washed with distilled water, dehydrated with ascending grades of ethanol and cleared with xylene and cover slipped with DPX mounting media.

Results

Hypoxia

Hypoxia is a condition where not enough oxygen makes it to the cells and tissues in the body. This can happen even though blood flow is normal. It can lead to many serious, sometimes life-threatening complications. Generally, lung cells experience hypoxia in acute and chronic lung diseases, during travel to high altitude, and during fetal development. Chronic hypoxia leads to increase in inflammation, alveolar degeneration leading to emphysema which is one of the causative factors for the development of COPD and ARDS. Hypoxia Inducible factor (HIF-1) signalling pathway is activated in COPD, and the overexpression of related proteins such as HIF-1α and VEGF is associated with a decrease of lung function, reduced quality of life and progression of COPD.

Recent evidence indicate that hypoxia is a primary pathophysiologic feature and main cause of mortality in patients with severe COVID-19 and it accompanies all the stages of the disease. The protein targets of HIF-1α are involved in the severe hypoxia-induced activation of proinflammatory cytokine expression and the subsequent inflammation process and cytokine storm phase of COVID-19.

Figure 1B:
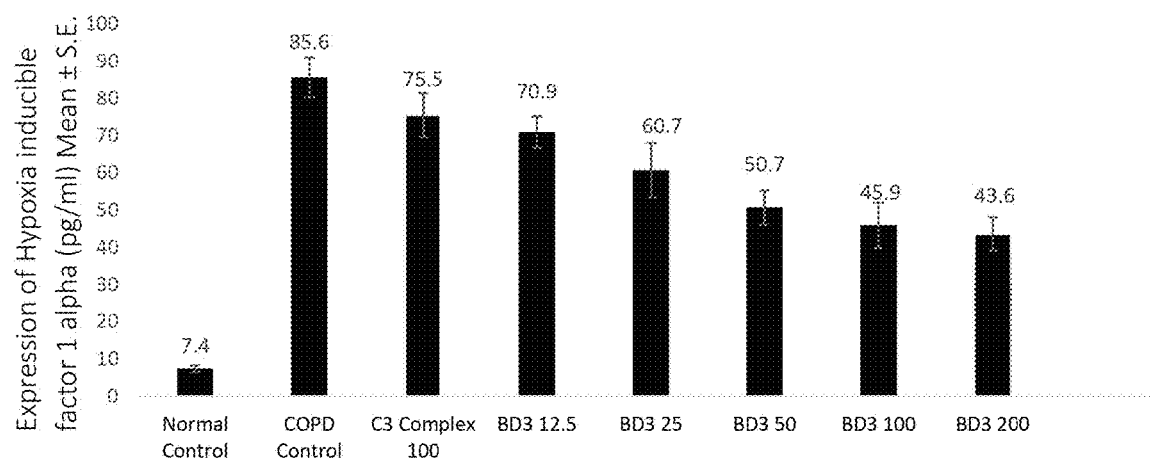
FIG. 1B is the graphical representation showing decrease in HIF-1α levels in COPD mice treated with varying doses (mg/kg bodyweight) of bisdemethoxycurcumin (BDMC) compared to curcumin and demethoxycurcumin (DMC).
Figure 1C:
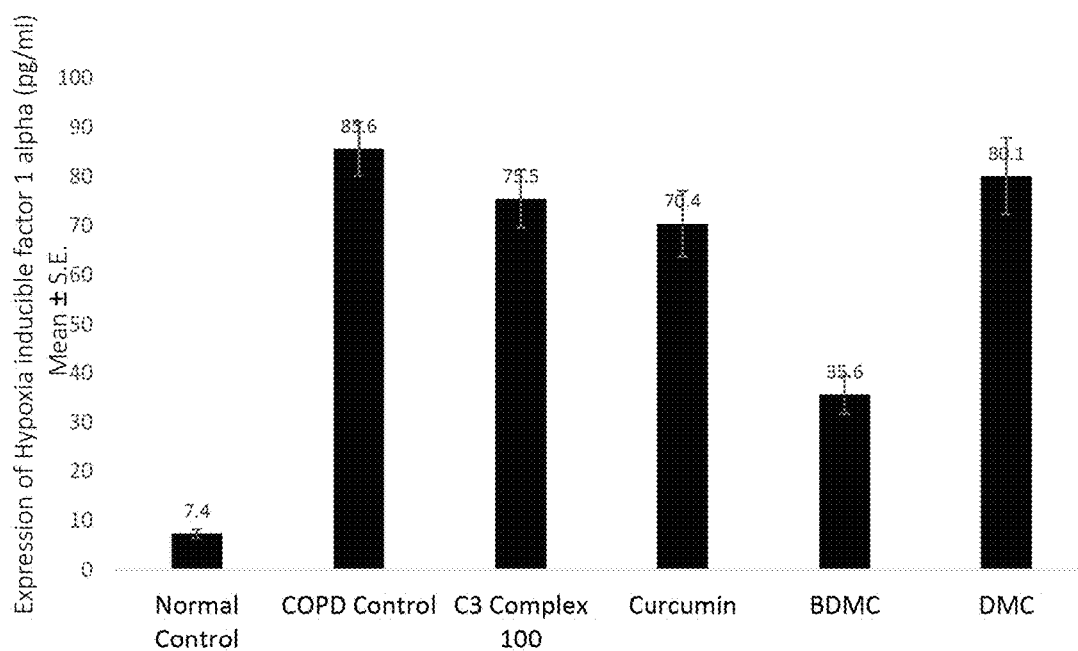
FIG. 1C is the graphical representation showing the dose dependant decrease in HIF-1α levels in COPD mice treated with varying doses (mg/kg bodyweight) of a composition comprising bisdemethoxycurcumin (BD3 complex) compared to curcumin C3 complex.

In the present study, the effect of BDMC on reducing the levels of HIF-1α was evaluated and compared with curcumin, DMC. The results indicated that BDMC decreased the levels of HIF-1α in a dose dependant manner (FIG. 1A). BDMC also very effective compared to curcumin and DMC (FIG. 1B), indicating the non-obvious effect of BDMC in reducing hypoxia. The composition comprising BDMC, curcumin and DMC (BD3 complex) was also effective in reducing hypoxia, by reducing the elevated levels of HIF-1α compared to Curcumin C3 complex (FIG. 1C).

Surfactant Proteins

Pulmonary surfactant is essential for life as it lines the alveoli to lower surface tension. The main functions of surfactant include 1) lowering surface tension at the air-liquid interface and thus preventing alveolar collapse at end-expiration, 2) interacting with and subsequent killing of pathogens and 3) modulating immune responses. Surfactant components are synthesized primarily by the alveolar type II cell, which synthesizes surfactant proteins SP-A, SP-B, and SP-D, collectively called Collectins. They bind to viruses, bacteria to facilitate pathogen removal. Host defense in the alveolar interface is extremely demanding since even moderate degrees of inflammation and exudation compromise gas exchange. As SP-A and SP-D are present in the mucus layer and alveolar surface, they are well positioned to prevent infection of epithelial cells through viral neutralization, agglutination, and enhanced phagocytosis. SP-A and/or SP-D bind to hemagglutinin and neuraminidase of influenza A virus to inhibit their activity. Pulmonary collectins also bind to glycoproteins of viruses, including HIV, Respiratory syncytial virus (RSV) and severe acute respiratory syndrome (SARS) coronavirus. The following documents disclose the importance of surfactant proteins, which is herein incorporated by reference:

1. Qi L et al. The ability of pandemic influenza virus hemagglutinins to induce lower respiratory pathology is associated with decreased surfactant protein D binding. Virology. 2011; 412:426/134.
2. Meschi J, et al. Surfactant protein D binds to human immunodeficiency virus (HIV) envelope protein gp120 and inhibits HIV replication. J Gen Virol. 2005; 86:3097-3107.
3. Hickling T P, et al. A recombinant trimeric surfactant protein D carbohydrate recognition domain inhibits respiratory syncytial virus infection in vitro and in vivo. Eur J Immunol. 1999; 29:3478-3484.
4. Leth-Larsen R et al. The SARS coronavirus spike glycoprotein is selectively recognized by lung surfactant protein D and activates macrophages. Immunobiology. 2007; 212:201-211.

Figure 2A:
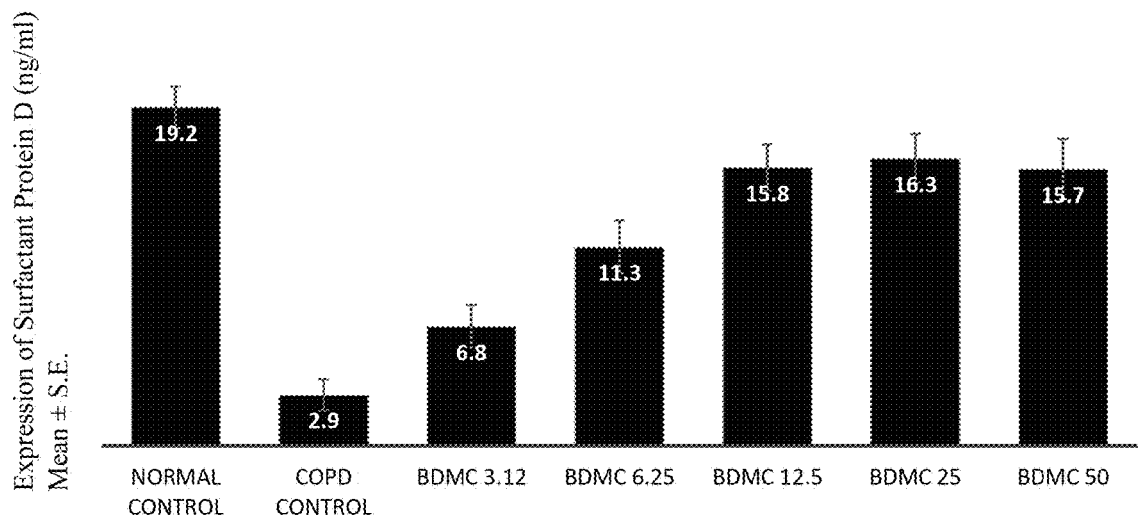
FIG. 2A is the graphical representation showing the dose dependant increase in surfactant protein D levels in COPD mice treated with varying doses (mg/kg bodyweight) of bisdemethoxycurcumin (BDMC) compared to normal and COPD control groups.
Figure 2B:
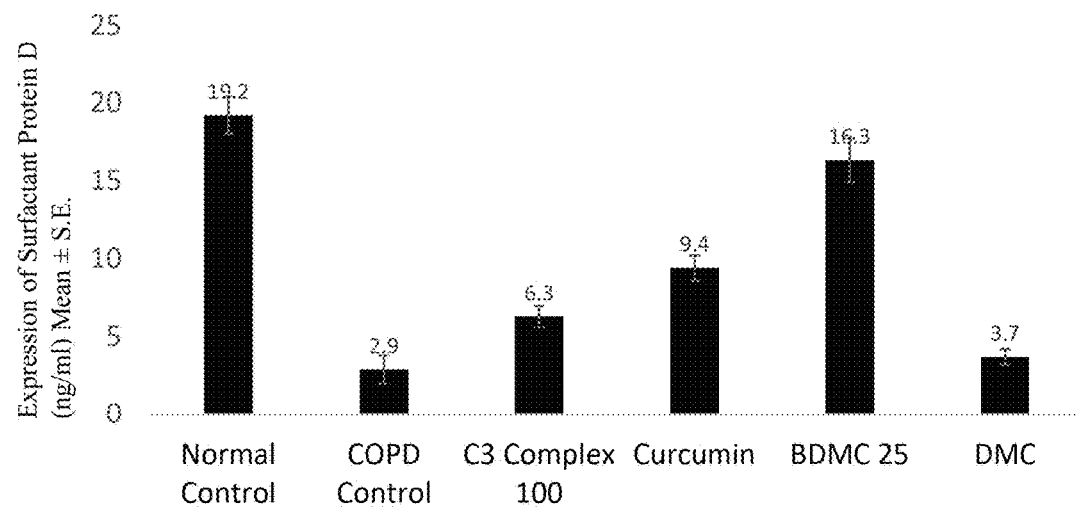
FIG. 2B is the graphical representation showing the dose dependant increase in surfactant protein D levels in COPD mice treated with varying doses (mg/kg bodyweight) of bisdemethoxycurcumin (BDMC) compared to curcumin and demethoxycurcumin (DMC).
Figure 2C:
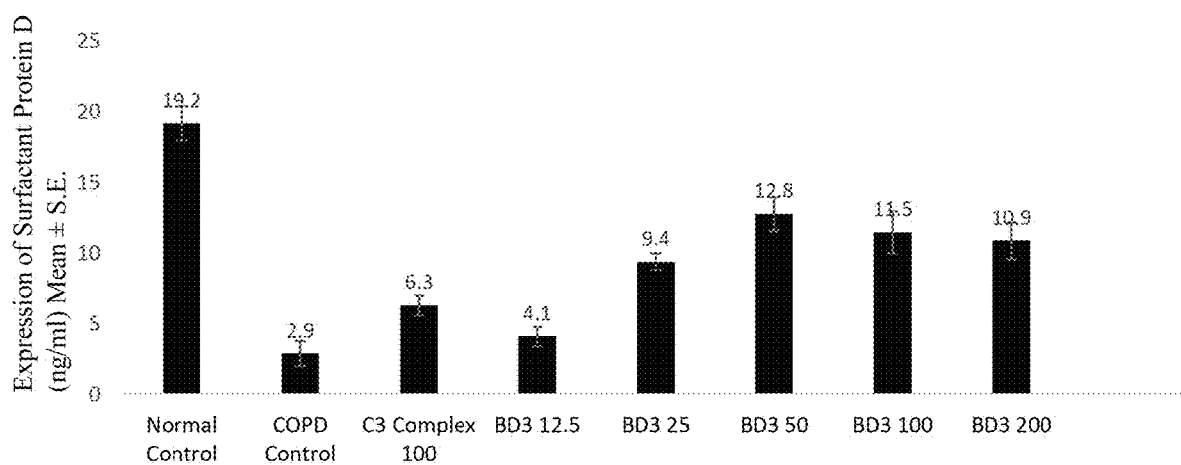
FIG. 2C is the graphical representation showing the dose dependant increase in surfactant protein D levels in COPD mice treated with varying doses (mg/kg bodyweight) of a composition comprising bisdemethoxycurcumin (BD3 complex) compared to curcumin C3 complex.

In the present study, the effect of BDMC on increasing the levels of surfactant protein D was evaluated and compared with curcumin, DMC. The results indicated that BDMC increase the levels of surfactant protein D in a dose dependant manner (FIG. 2A). BDMC also very effective compared to curcumin and DMC (FIG. 2B), indicating the non-obvious effect of BDMC. The composition comprising BDMC, curcumin and DMC (BD3 complex) was also effective in increasing the levels of surfactant protein D compared to Curcumin C3 complex (FIG. 2C).

Periostin

Pulmonary capillary leakage followed by influx of blood fluid into the air space of lung alveoli is a crucial step in the progression of lung injury. This influx is due to increased permeability of the alveolar-capillary barrier. The extracellular matrix (ECM) between the capillary and the epithelium is involved in prevention of the influx and the ECM architecture is organized by periostin, a matricellular protein localized in the alveolar walls. The binding sites on periostin contributes to the mechanical strength of connective tissues. It enhances intermolecular interactions in close proximity and their assembly into extracellular matrix architectures.

Figure 3A:
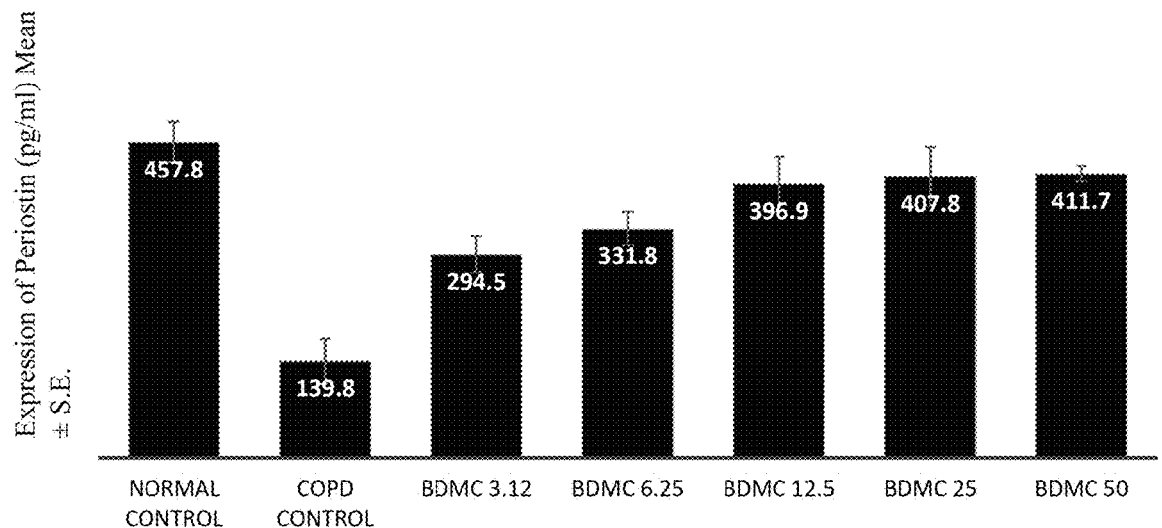
FIG. 3A is the graphical representation showing the dose dependant increase in periostin levels in COPD mice treated with varying doses (mg/kg bodyweight) of bisdemethoxycurcumin (BDMC) compared to normal and COPD control groups.
Figure 3B:
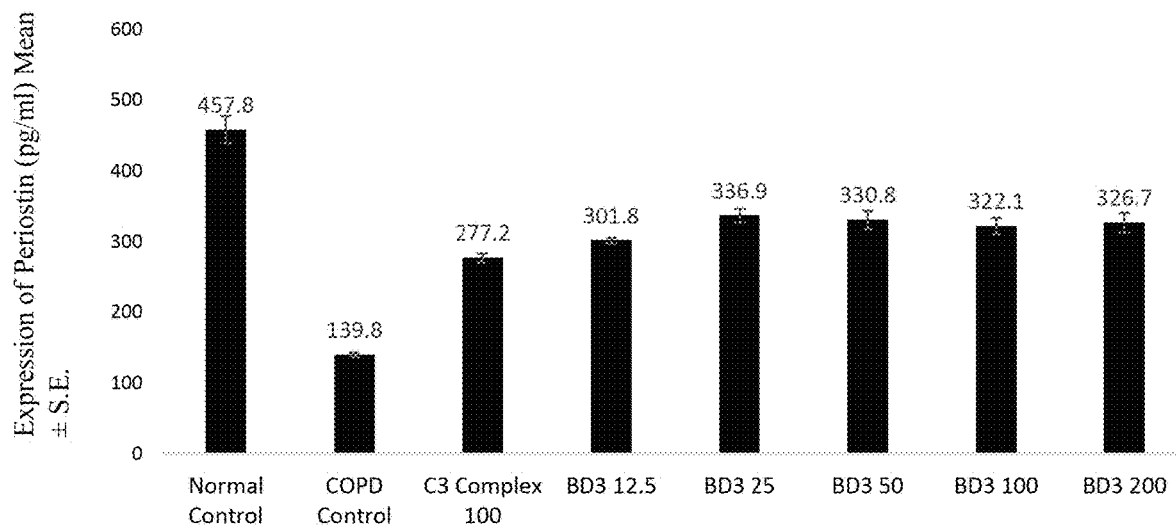
FIG. 3B is the graphical representation showing the dose dependant increase in periostin levels in COPD mice treated with varying doses (mg/kg bodyweight) of a composition comprising bisdemethoxycurcumin (BD3 complex) compared to curcumin C3 complex.

In the present study, the levels of periostin were significantly reduced in COPD. BDMC increase the levels of periostin in a dose dependant manner (FIG. 3A). The composition comprising BDMC, curcumin and DMC (BD3 complex) was also effective in increasing the levels of periostin compared to Curcumin C3 complex (FIG. 3B).

12 and 15 Lipoxygenase in Alveolar Damage

Accumulation and recruitment of neutrophils to the lung are key events in the development of Lung injury. Neutrophil recruitment to the lung occurs in a cascade-like process of activation, intravascular accumulation, and transendothelial and transepithelial migration. 12/15-LOX modulates neutrophil recruitment into the lung by regulating chemokine/chemokine receptor homeostasis. It also generates lipid mediators with immune modulatory properties by enzymatic oxidation of polyunsaturated fatty acids. It is reported that controlled and timed 12/15-LOX expression can facilitate the resolution of inflammation. Its deregulated activity, however, contributes to tissue damage, cell death and chronic inflammation.

Figure 4A:
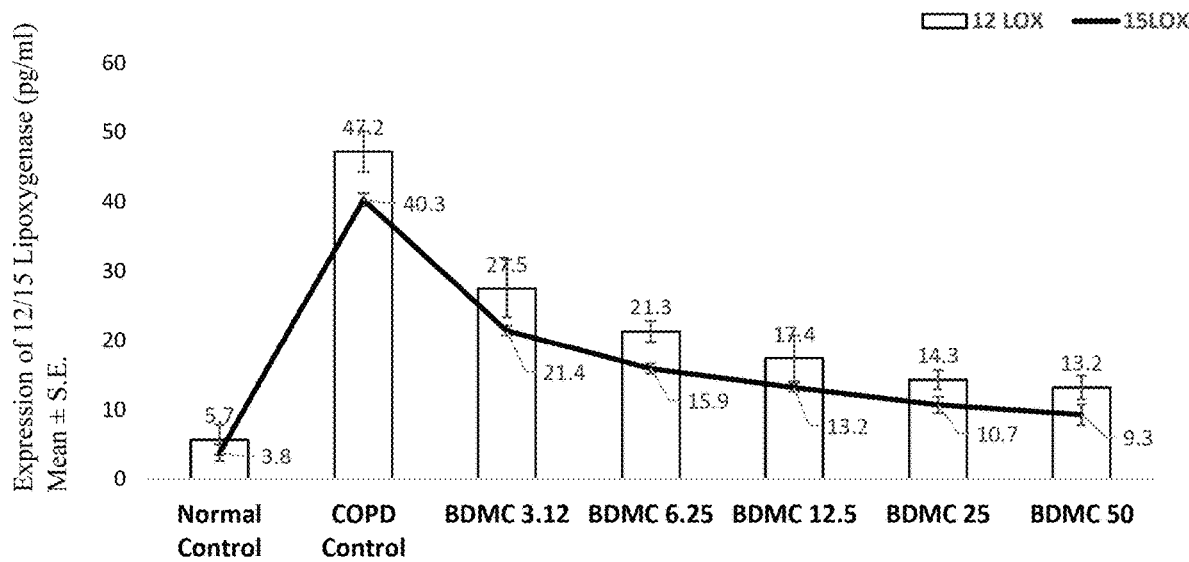
FIG. 4A is the graphical representation showing the dose dependant decrease in 12/15-LOX levels in COPD mice treated with varying doses (mg/kg bodyweight) of bisdemethoxycurcumin (BDMC) compared to normal and COPD control groups. The values in the bar represent 12 LOX and the line represent 15 LOX
Figure 4B:
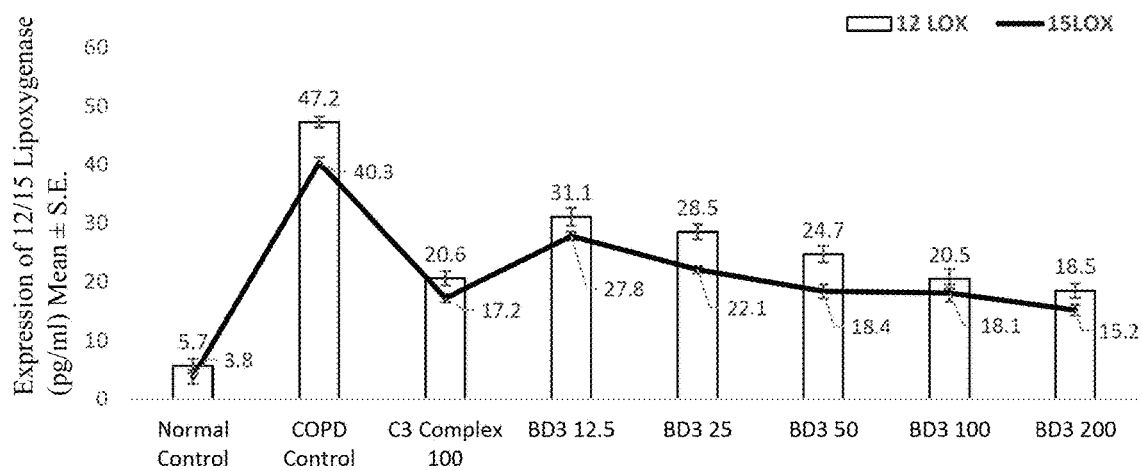
FIG. 4B is the graphical representation showing the dose dependant decrease in 12/15-LOX levels in COPD mice treated with varying doses (mg/kg bodyweight) of a composition comprising bisdemethoxycurcumin (BD3 complex) compared to curcumin C3 complex. The values in the bar represent 12 LOX and the line represent 15 LOX

In the present study, the levels of 12/15-LOX were significantly elevated in COPD. BDMC decreased the levels of 12/15-LOX in a dose dependant manner (FIG. 4A). The composition comprising BDMC, curcumin and DMC (BD3 complex) was also effective in decreasing the levels of 12/15-LOX (FIG. 4B).

Bradykinin

Bradykinin is a physiologically and pharmacologically active peptide of the kinin group of proteins, consisting of nine amino acids. It is a potent endothelium-dependent vasodilator and mild diuretic, which causes lowering of the blood pressure. It also causes contraction of non-vascular smooth muscle in the bronchus and gut, increases vascular permeability and is also involved in the mechanism of pain.

Figure 5A:
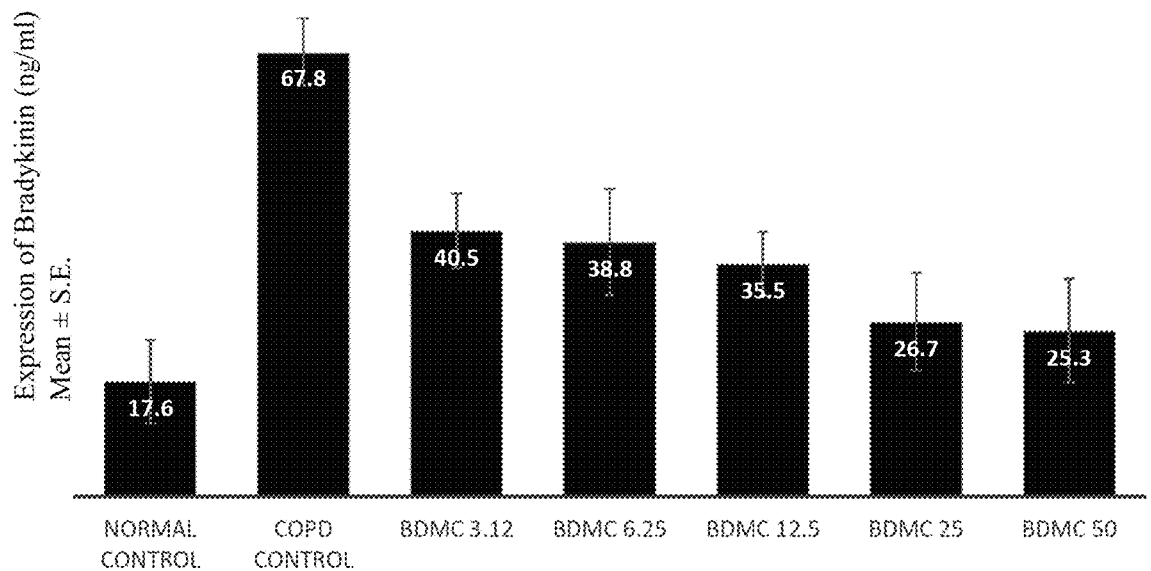
FIG. 5A is the graphical representation showing the dose dependant decrease in bradykinin levels in COPD mice treated with varying doses (mg/kg bodyweight) of bisdemethoxycurcumin (BDMC) compared to normal and COPD control groups.
Figure 5B:
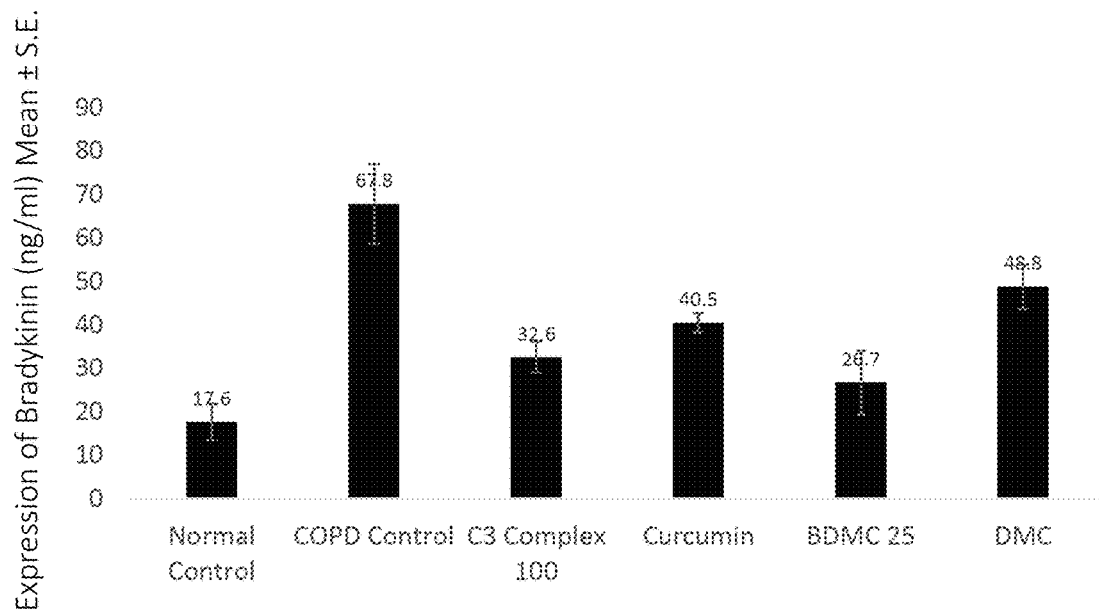
FIG. 5B is the graphical representation showing decrease in bradykinin levels in COPD mice treated with varying doses (mg/kg bodyweight) of bisdemethoxycurcumin (BDMC) compared to curcumin and demethoxycurcumin (DMC).
Figure 5C:
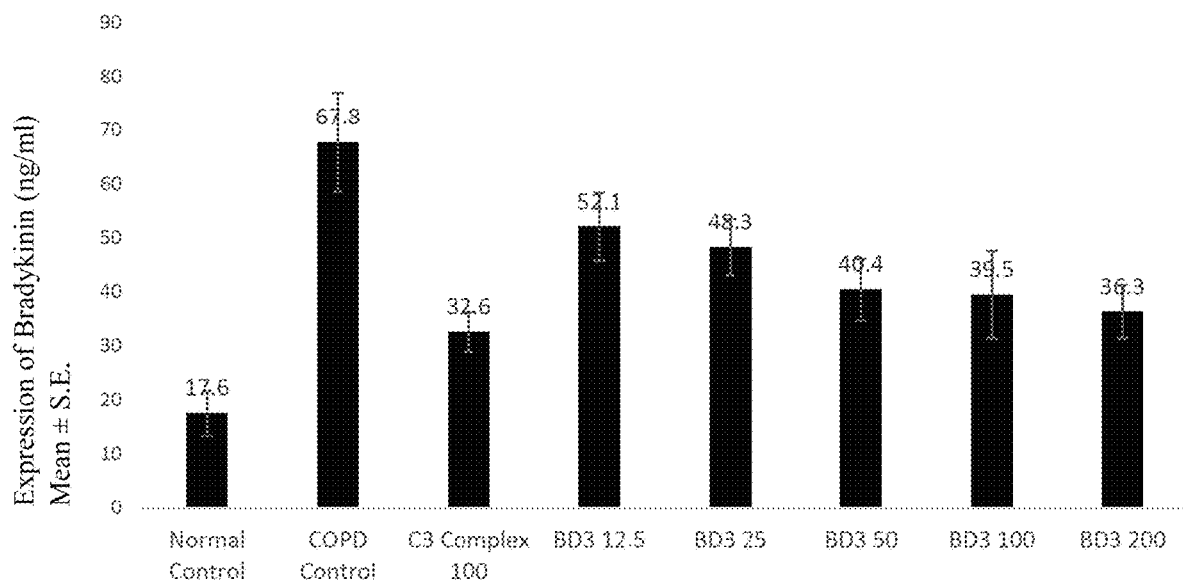
FIG. 5C is the graphical representation showing the dose dependant decrease in bradykinin levels in COPD mice treated with varying doses (mg/kg bodyweight) of a composition comprising bisdemethoxycurcumin (BD3 complex) compared to curcumin C3 complex FIG. 6 A is the graphical representation showing the dose dependant decrease in IL-17 and IL-23 levels in COPD mice treated with varying doses (mg/kg bodyweight) of bisdemethoxycurcumin (BDMC) compared to normal and COPD control groups.

In the present study, the levels of Bradykinin was significantly elevated in COPD, indicating increase vascular permeability, inflammation and pain. BDMC decreased the levels of Bradykinin in a dose dependant manner (FIG. 5A). BDMC was also very effective compared to curcumin and DMC in reducing the elevated levels of bradykinin (FIG. 5B). The composition comprising BDMC, curcumin and DMC (BD3 complex) was also effective in decreasing bradykinin levels (FIG. 5C), thereby decreasing pain, inflammation and vascular permeability.

Immune Markers IL-1, IL-23 and IL-6

There are increased numbers of activated T lymphocytes in the bronchial mucosa of COPD patients. T helper type 17 (Th17) cells are reported to release interleukin (IL)-17 as their effector cytokine under the control of IL-22 and IL-23. This, in turn, plays a role in inducing neutrophils and tissue re-modelling in the bronchi of the patients. Overexpression of IL-17 in murine lung epithelium induces lung inflammation with a COPD-like phenotype involving recruitment of CD4 cells, mucus hypersecretion and small airways fibrosis. It also causes induction of the expression of many chemokines (including CXCL1 and CXCL 8) and matrix metalloproteinase-9.

Figure 6A:
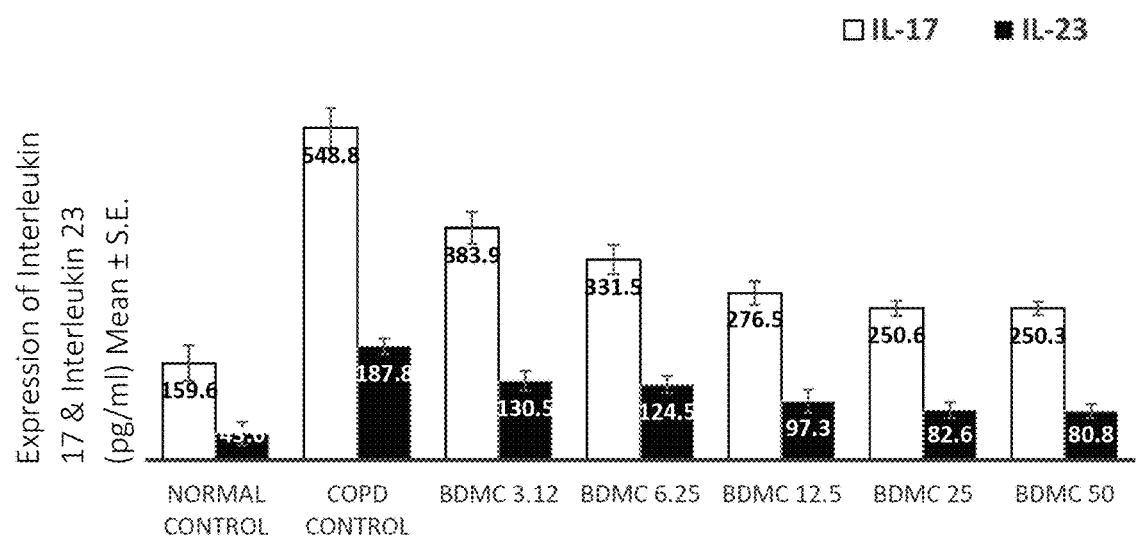
FIG. 6 B is the graphical representation showing the dose dependant decrease in IL-17 and IL-23 levels in COPD mice treated with varying doses (mg/kg bodyweight) of a composition comprising bisdemethoxycurcumin (BD3 complex) compared to curcumin C3 complex.
Figure 6B:
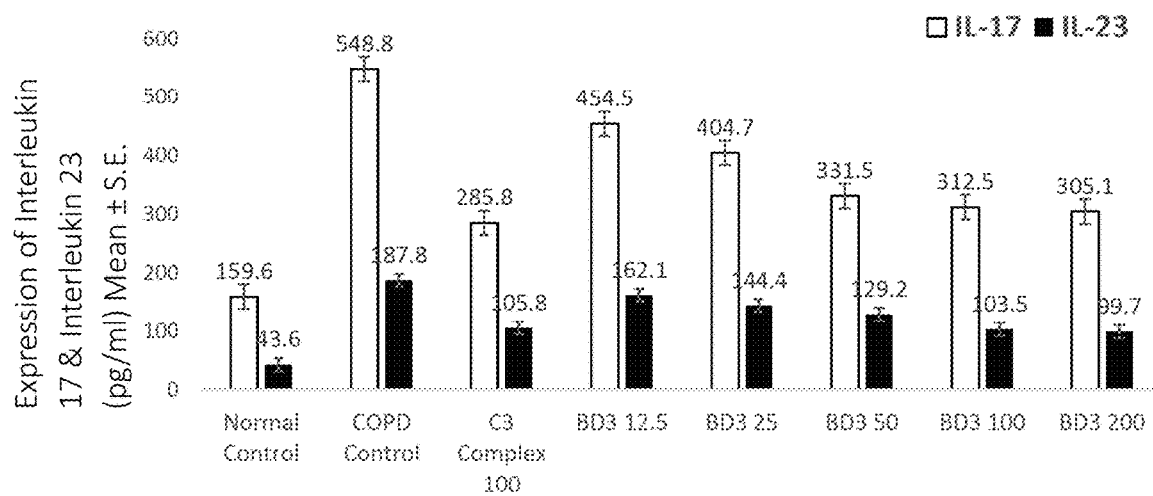
Figure 7A:
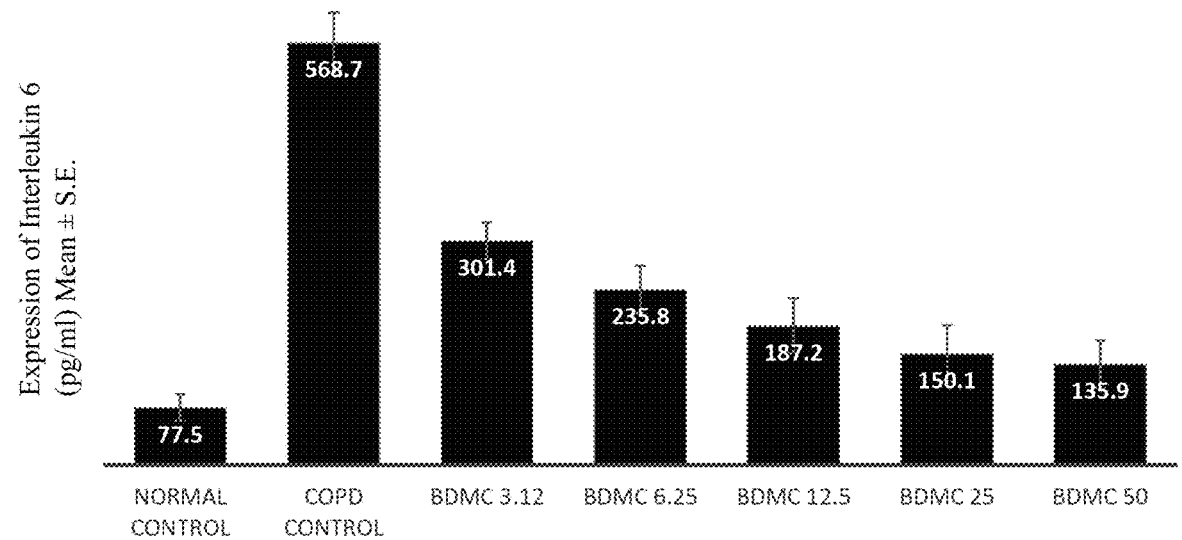
FIG. 7 A is the graphical representation showing the dose dependant decrease in IL-6 levels in COPD mice treated with varying doses (mg/kg bodyweight) of bisdemethoxycurcumin (BDMC) compared to normal and COPD control groups.
Figure 7B:
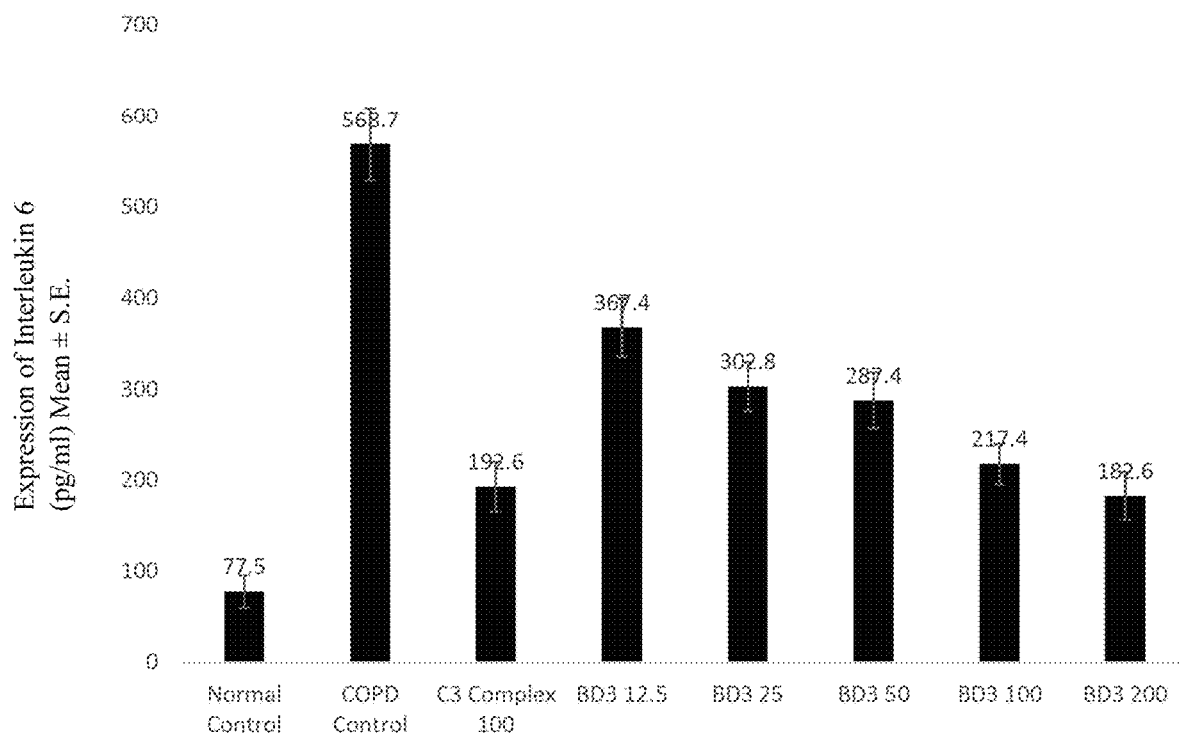

There is substantial evidence indicating the presence of neutrophilic inflammation in COPD. Cigarette smoke, oxidative stress, bacteria and viruses activate neutrophilic inflammation via nuclear factor-κB (NF-κB) signalling in airway epithelial cells. Macrophages are also activated and attract Th17 cells to release IL-17, which stimulates the release of IL-6 and CXCL8 from epithelial cells. Neutrophils release neutrophil elastase, which is a potent inducer of mucus secretion. Neutrophils also generate oxidative stress, which further activates inflammation and induces corticosteroid resistance In the present study, the levels of IL-17 and IL-23 were significantly elevated in COPD, indicating increased neutrophilic inflammation. BDMC decreased the levels of these inflammatory markers in a dose dependant manner (FIG. 6A). The composition comprising BDMC, curcumin and DMC (BD3 complex) was also effective in decreasing IL-17 and IL-23 levels (FIG. 6B), thereby reducing inflammation and influx cytokines and chemokines. The levels of IL-6 was significantly elevated in COPD. BDMC and BD3 complex decreased the levels of IL6 in a dose dependant manner (FIGS. 7A and 7B).

Elevated Inflammatory Chemokines in COPD

Figure 8A:
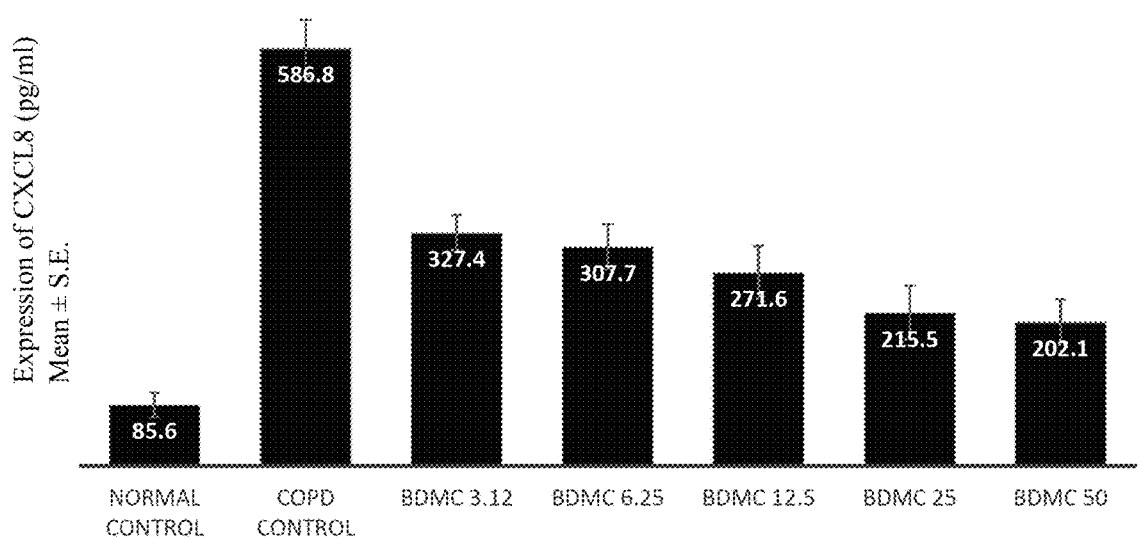
FIG. 8 A is the graphical representation showing the dose dependant decrease in CXCL8 levels in COPD mice treated with varying doses (mg/kg bodyweight) of bisdemethoxycurcumin (BDMC) compared to normal and COPD control groups.
Figure 8B:
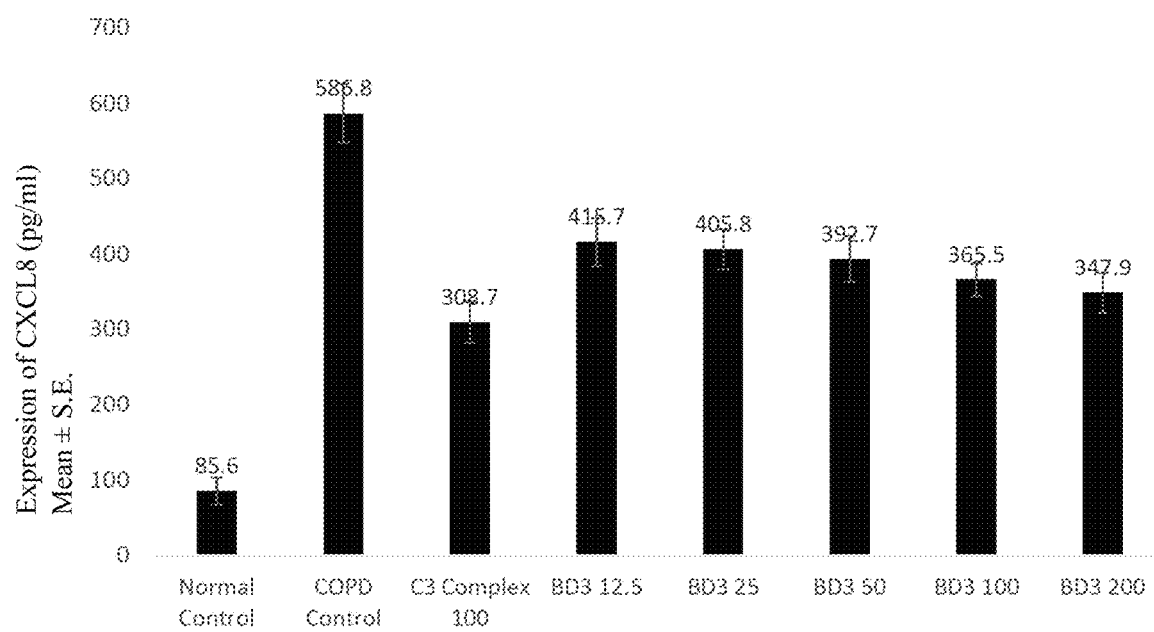

Chemokines released from epithelial cells and macrophages in the lung recruit inflammatory cells from the circulation leading to the development of COPD. The inflammatory-cell trafficking orchestrated by multiple chemokines, blocked with selective antagonists is an effective anti-inflammatory strategy in this disease. In the present study, the levels of CXCL8 were significantly elevated in COPD, indicating increased inflammation and chemokine influx. BDMC decreased the levels of these CXCL8 in a dose dependant manner (FIG. 8A). The composition comprising BDMC, curcumin and DMC (BD3 complex) was also effective in decreasing CXCL8 levels (FIG. 8B), thereby reducing inflammation.

Lactate Dehydrogenase

Lactate dehydrogenase (LDH) is the enzyme that catalyses the final step in the glycolytic metabolism, regenerating NAD+ from reduced NADH, by conversion of pyruvate to lactate. If cell lysis occurs, or cell membranes are damaged, cytoplasmic enzymes, such as LDH are released into the extracellular space. Increased muscle LDH activity has been found in elderly male patients with COPD who were susceptible to contractile fatigue.

Figure 9A:
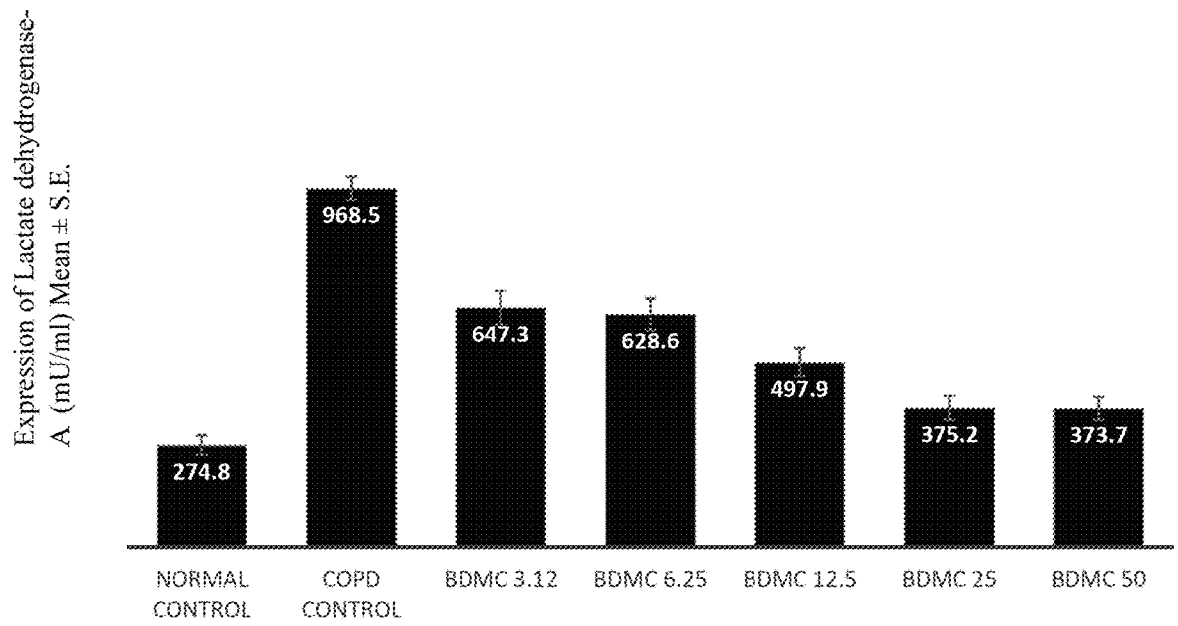
FIG. 9 A is the graphical representation showing the dose dependant decrease in LDH levels in COPD mice treated with varying doses (mg/kg bodyweight) of bisdemethoxycurcumin (BDMC) compared to normal and COPD control groups.
Figure 9B:
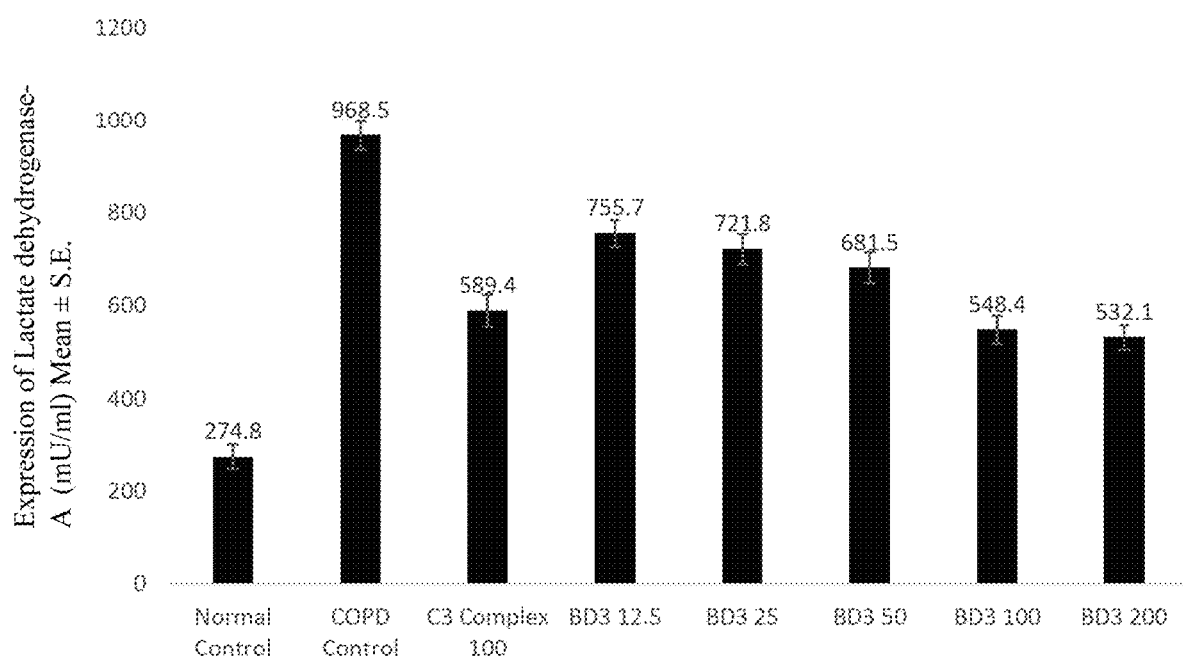

In the present study, the levels of LDH were significantly elevated in COPD group, indicating increased muscle damage and fatigue. BDMC decreased the levels of these LDH in a dose dependant manner (FIG. 9A). The composition comprising BDMC, curcumin and DMC (BD3 complex) was also effective in decreasing LDH levels (FIG. 9B).

Immunohistochemistry

Figure 10:
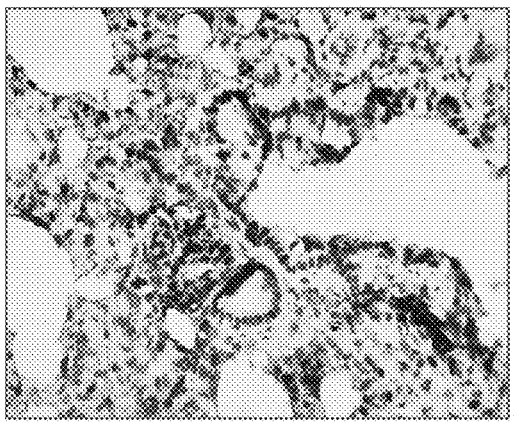
FIG. 10 is the immunohistochemical staining image of lung tissue sections of normal mice, COPD mice and mice treated with 25 mg/kg and 100 mg/kg BDMC, showing regeneration of alveolar type II cells.
Figure 10:
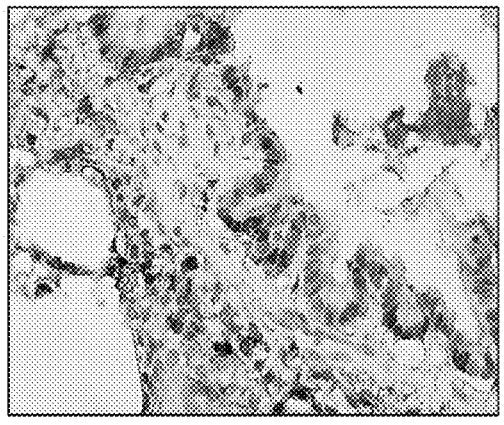
Figure 10:
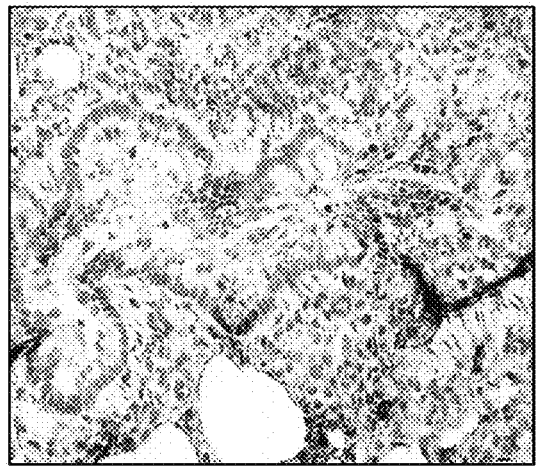
Figure 10:
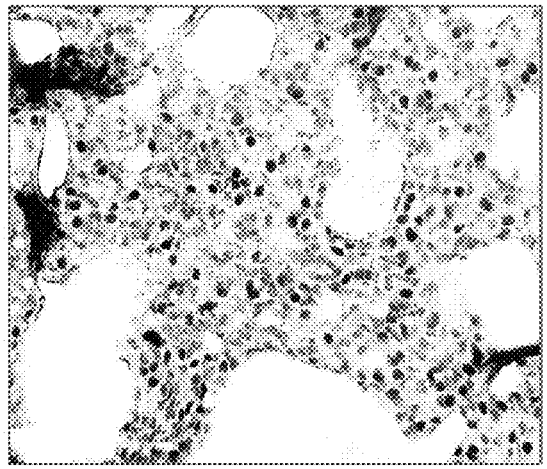

The immunohistochemistry was performed as per protocol and the cells were stained and visualised. In the normal control group, the lesion tissue showed normal histoarchitecture with lung alveoli and bronchial epithelium. The tissue Type 2 Alveolar epithelium with positive intra-nuclear staining. An even distribution of type-II cells was seen in the alveoli and bronchial lining cells. However, in the COPD group, the lesion tissue showed diffuse thickening of alveolar septa characterized by intense infiltration of mononuclear cells. The alveoli remained distorted. The number alveolar type-II positive cells were nil/negligible when compared with Normal control Group. The bronchial epithelium also showed occasional positive type II cells, indicating increased degeneration of alveoli. In The lesion tissue in groups treated with 25 mg/kg bodyweight showed diffuse thickening of alveolar septa with infiltration of mononuclear cells. Although the alveoli remained distorted throughout the tissue section, the alveolar type II positive cells were seen in a diffuse manner throughout the parenchyma. There was a significant increase in number of type II positive cells when compared to disease control Group. Further in group of mice treated with 100 mg/kg bodyweight BDMC, the lesion tissue showed diffuse thickening of alveolar septa with infiltration of mononuclear cells. The alveoli remained distorted throughout the tissue section. The type II positive cells were mild to moderately high when compared with disease control. Occasionally bronchial epithelium showed type II positive cells, indicated regeneration of alveoli, damaged due to emphysema and COPD (FIG. 10)

Overall, the results suggest that BDMC per se and the composition comprising BDMC (BD3 complex) decreased the activation of tissue macrophage, reduced hypoxia, decreased proinflammatory cytokines, chemokines and bradykinin thereby regenerating alveolar type II cells by restoring alveolar capillary barrier. The composition is very suitable for treating COPD and ARDS due to viral infections, specifically COVID 19 and for improving lung function during prognosis.

Other modifications and variations of the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention and is to be interpreted only in conjunction with the appended claims.

We claim:

1. A method for regeneration of alveolar cells in mammals with emphysema associated with chronic obstructive pulmonary disease, said method comprising step of administering a composition comprising not less than 20% w/w bisdemethoxycurcumin to said mammals to bring about a reduction in features of emphysema.

2. The method as in claim 1, wherein the composition further comprises 10-35% w/w demethoxycurcumin and 10-45% w/w curcumin.

3. The method as in claim 1, wherein the features of emphysema are selected from the group consisting of hypoxia, decreased levels of lung surfactant proteins, increased permeability of the alveolar-capillary barrier, inflammation, increased accumulation and recruitment of neutrophils, elevated alveolar pressure, increased oxidative stress, elevated inflammatory cytokines and chemokines, increased numbers of activated T lymphocytes and muscle damage.

4. The method as in claim 1, wherein emphysema is induced by enzymes, viruses, bacteria, smoke and particulate irritants.

5. The method as in claim 1, wherein the mammal is human.

6. A method of therapeutic management of chronic obstructive pulmonary disease in mammals, said method comprising step of administering a composition comprising not less than 20% w/w bisdemethoxycurcumin to said mammals to bring about a reduction in features and symptoms of chronic obstructive pulmonary disease.

7. The method as in claim 6, wherein the composition further comprises 10-35% w/w demethoxycurcumin and 10-45% w/w curcumin.

8. The method as in claim 6, wherein the chronic obstructive pulmonary disease is emphysematous and non-emphysematous.

9. The method as in claim 6, wherein the features of chronic obstructive pulmonary disease are selected from the group consisting of hypoxia, decreased levels of lung surfactant proteins, increased permeability of the alveolar-capillary barrier, inflammation, increased accumulation and recruitment of neutrophils, elevated alveolar pressure, increased oxidative stress, elevated inflammatory cytokines and chemokines, increased numbers of activated T lymphocytes and muscle damage.

10. The method as in claim 6, wherein symptoms of chronic obstructive pulmonary disease are selected from the group consisting of shortness of breath, especially during physical activities, wheezing, chest tightness, chronic cough that may produce mucus, respiratory infections, lack of energy, unintended weight loss, and swelling in ankles, feet or legs.

11. The method as in claim 6, wherein chronic obstructive pulmonary disease is induced by enzymes, viruses, bacteria, smoke and particulate irritants.

12. The method as in claim 6, wherein the mammal is human.

* * * * *